United States Patent
Yanai et al.

(10) Patent No.: US 8,652,024 B1
(45) Date of Patent: Feb. 18, 2014

(54) STERILIZABLE CABLE SYSTEM FOR IMPLANTABLE BLOOD PUMP

(71) Applicant: Thoratec Corporation, Pleasanton, CA (US)

(72) Inventors: Masamichi Yanai, Ann Arbor, MI (US); J. Bradford Rainier, Chelsea, MI (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/747,675

(22) Filed: Jan. 23, 2013

(51) Int. Cl.
*A61N 1/362* (2006.01)

(52) U.S. Cl.
USPC .......................................................... 600/16

(58) Field of Classification Search
USPC .......................................................... 600/16
See application file for complete search history.

(56) References Cited

U.S. PATENT DOCUMENTS

| | | | |
|---|---|---|---|
| 4,895,557 A * | 1/1990 | Moise et al. | ..................... 600/16 |
| 2010/0256440 A1 | 10/2010 | Maher et al. | |
| 2011/0298304 A1 | 12/2011 | Cotter | |

* cited by examiner

*Primary Examiner* — George Manuel
(74) *Attorney, Agent, or Firm* — Kilpatrick Townsend and Stockton

(57) ABSTRACT

A implantable blood pump system includes a pump unit, a first percutaneous cable section, a control unit, and a second cable section connecting the control unit to the first cable section. All components except the control unit are sterilized. The connection between cable sections is removable. The connection between the control unit and second cable section is unremovable once it is assembled. The second cable section has a length sufficient to place an end outside of the sterile field for mating with the control unit during implantation.

7 Claims, 3 Drawing Sheets

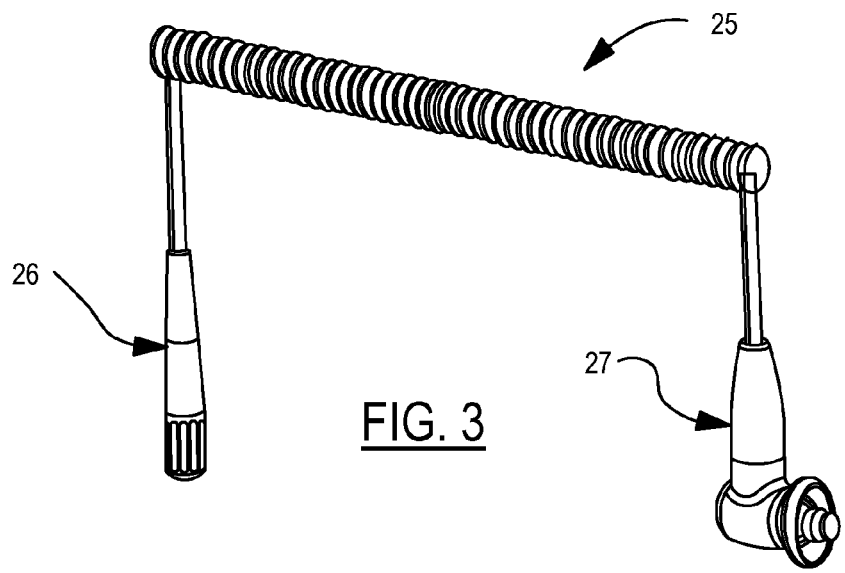
FIG. 3
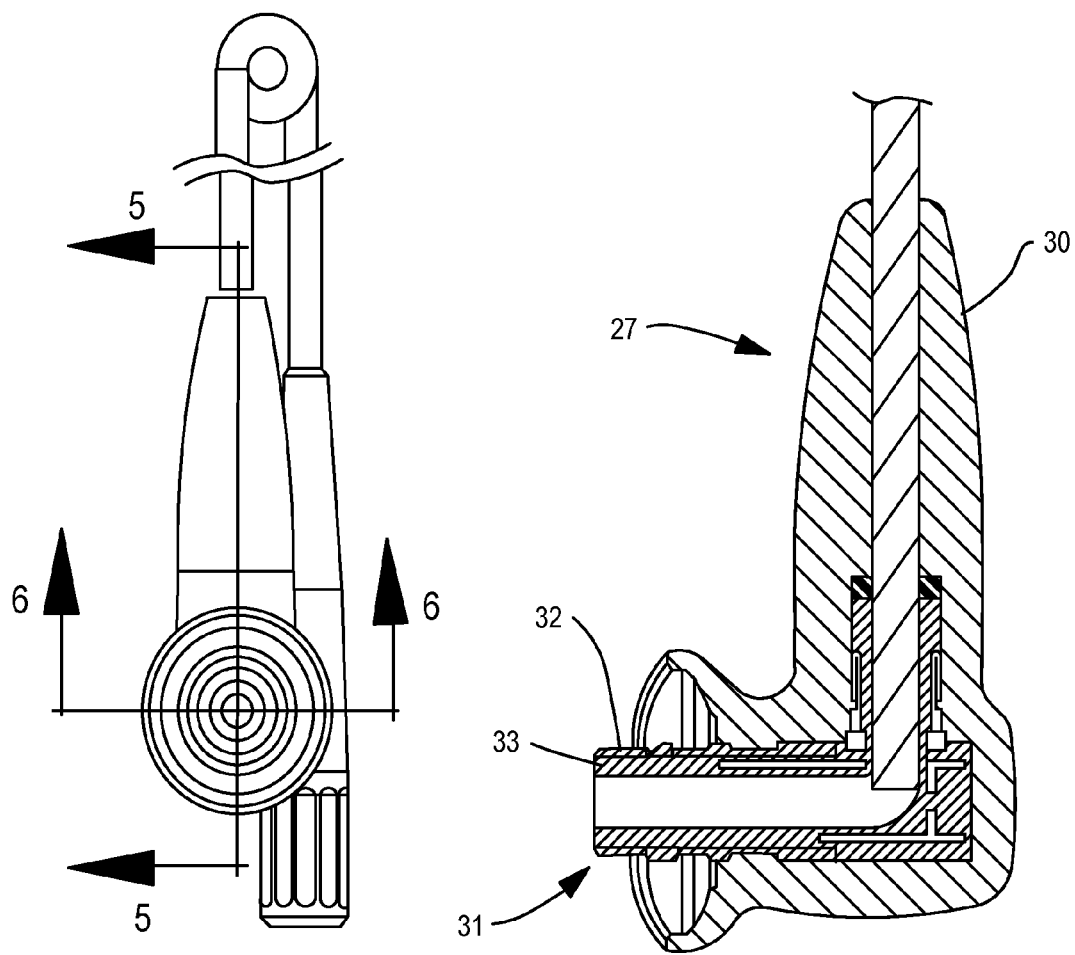
FIG. 4
FIG. 5

STERILIZABLE CABLE SYSTEM FOR IMPLANTABLE BLOOD PUMP

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to circulatory assist devices, and, more specifically, to preventing contamination of the surgical field during an implantation procedure while avoiding the need to sterilize an external control unit.

Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart, Inc., of Ann Arbor, Mich. The DuraHeart® system employs a centrifugal pump with a magnetically levitated impeller to pump blood from the left ventricle to the aorta. An electric motor magnetically coupled to the impeller is driven at a speed appropriate to obtain the desired blood flow through the pump.

A typical cardiac assist system includes a pumping unit, electrical motor (e.g., a brushless DC motor integrated in the pump housing), drive electronics, microprocessor control unit, and an energy source such as rechargeable batteries and/or an AC power conditioning circuit. The system is implanted during a surgical procedure in which a centrifugal pump is placed in the patient's chest. An inflow conduit is pierced into the left ventricle to supply blood to the pump. One end of an outflow conduit is mechanically fitted to the pump outlet and the other end is surgically attached to the patient's ascending aorta by anastomosis. A percutaneous cable connects to the pump, exits the patient through an incision, and connects to the external control unit. For practical reasons, it is preferable that the percutaneous cable extends for only a short distance from the incision. A cable connector is provided at the end of the percutaneous cable in order to connect with an extension cable coming from the external controller.

As in any surgical procedure, it is necessary to maintain sterility within a sterile field during implantation of the LVAD. Sterility is required not only for the region around the surgical incisions and the components being implanted, but also for any objects entering or partially entering the field.

In the event of any problems or failure of the external control unit, it may become necessary to replace it. Therefore, a removable connection between the control unit and the percutaneous cable is employed. When the removable connection is provided at the connection between the percutaneous cable and the extension cable from the external unit (i.e., the extension cable is permanently fixed to the external control unit), then the control unit itself must be sterilized for the implantation procedure. In order for the control unit to be sterilizable, it must be airtight. Therefore, making a sterilizable control unit undesirably increases the cost of manufacture.

Alternatively, a make/break connection between the control unit and the extension cable may be provided such that the control unit does not enter the sterile field during implantation. If the extension cable is fully sterilized but extends outside the sterile field in order to be connected with the control unit outside the sterile field, then safety is maintained. However, the resulting system has a configuration subject to the disadvantage that in the event that it later becomes necessary to replace the control unit then there are two breakable connections to deal with (i.e., at either end of the extension cable). The possibility of two different connections can be confusing to users during an exchange of control units. It is desirable that only one possible disconnection/reconnection should be presented to the user when making such an exchange.

SUMMARY OF THE INVENTION

In one aspect of the invention, a blood pump system comprises a pump configured for implantation in a patient. A first cable section is configured to pass percutaneously through an incision in the patient having a first end connectable to the pump and having a second end with a first connector element. A second cable section has a first end with a second connector element and has a second end with a third connector element, wherein the second connector element removably mates with the first connector element. A control unit has a fourth connector element that mates with the third connector element. The first and second cable sections have been sterilized and the control unit is unsterilized. The third and fourth connector elements are unremovable after being mated.

BRIEF DESCRIPTION OF THE DRAWINGS

FIG. 3 is a perspective view of an extension cable according to one embodiment of the present invention.

FIG. 4 is an end view of the cable of FIG. 3.

FIG. 5 is a cross-sectional view of a one-time makeable connector element along line 5-5 of FIG. 4.

DETAILED DESCRIPTION OF PREFERRED EMBODIMENTS

Figure 1:
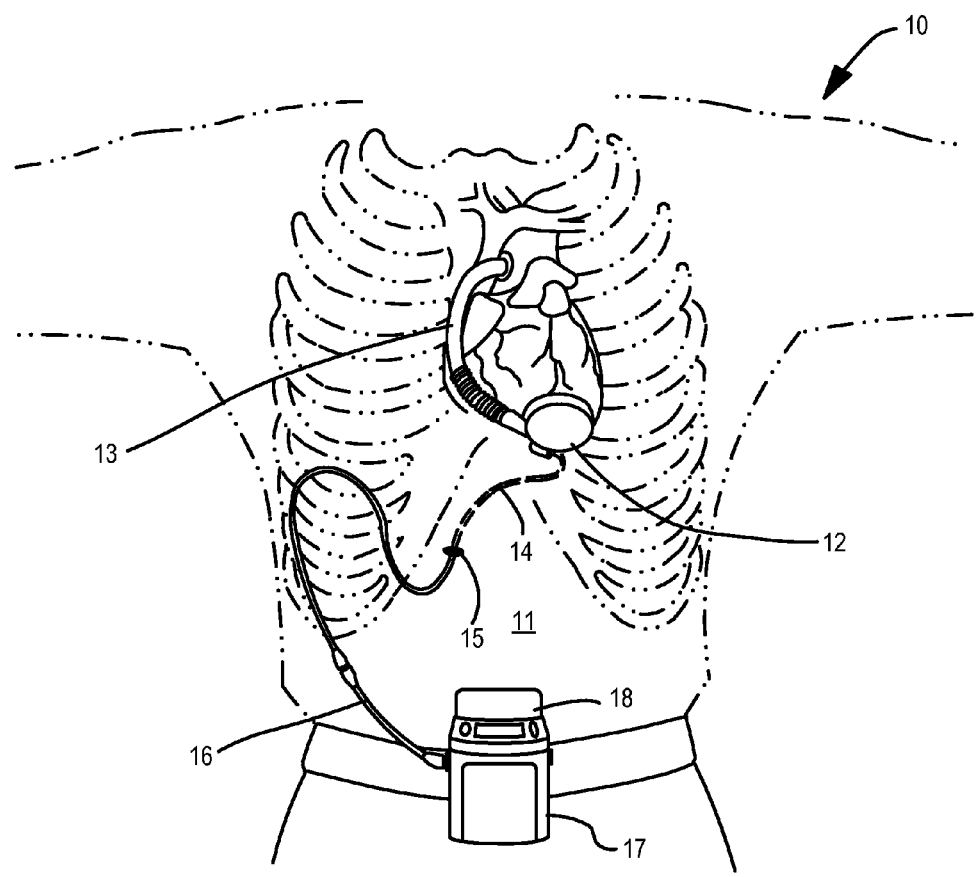
FIG. 1 is a diagram of a circulatory assist system as one example of an implantable pump employing the present invention.

Referring to FIG. 1, a patient 10 is shown in fragmentary front elevational view. Surgically implanted either into the patient's abdominal cavity or pericardium 11 is the pumping unit 12 of a ventricular assist device. An inflow conduit (on the hidden side of unit 12) pierces the heart to convey blood from the patient's left ventricle into pumping unit 12. An outflow conduit 13 conveys blood from pumping unit 12 to the patient's ascending thoracic aorta. A percutaneous power/communication cable 14 extends from pumping unit 12 outwardly of the patient's body via an incision 15 to an extension cable 16 which further connects to a control unit 17 worn by patient 10. Control unit 17 is powered by a main battery pack 18 and/or an external AC power supply and an internal backup battery.

Figure 2:
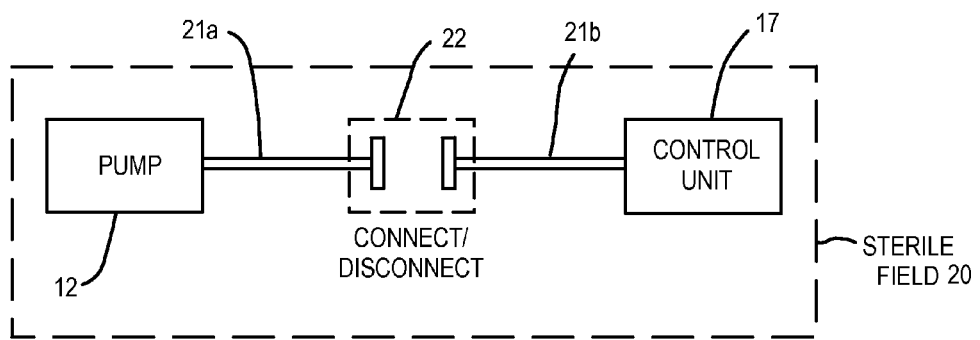
FIG. 2 is a block diagram showing a sterile field during implantation of a prior art assist system requiring sterilization of the control unit.
Figure 6:
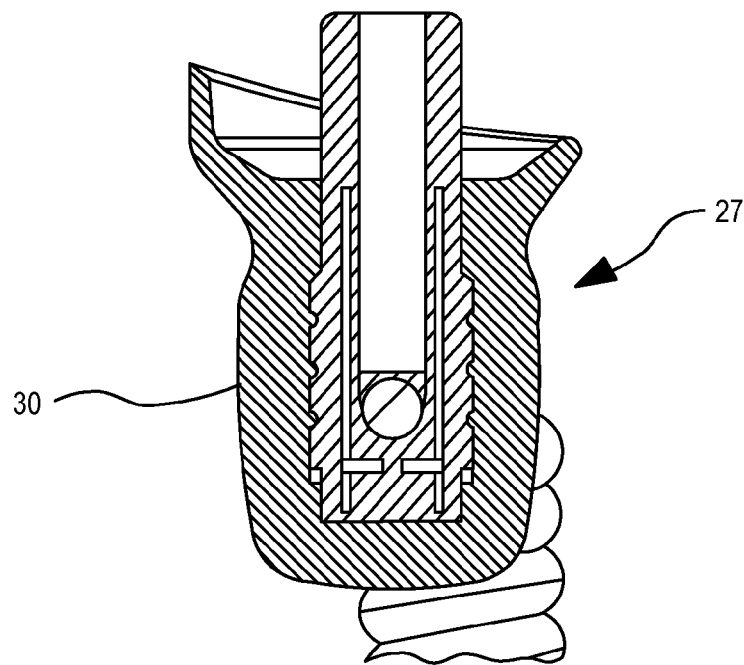
FIG. 6 is a cross-sectional view of the one-time makeable connector element along line 6-6 of FIG. 4.

FIG. 2 shows a sterile field 20 around a pump 12 and control unit 17 during an implantation procedure. A cable 21 between pump 12 and control unit 17 includes a percutaneous portion 21a and an external portion 21b separated by a removable connector 22 for connection during the implantation procedure. Connector 22 enables the subsequent disconnect and reconnection if it becomes necessary to replace control unit 17 at a later time. A pre-made, permanent connection between cable section 21b and control unit 17 results in the need for sterilization of control unit 17 since it must then be treated as occupying sterile field 20.

The present invention overcomes the need for sterilizing the control unit by employing an extension cable 25 as shown in FIG. 3 having a removable connector element 26 at one end and an unremovable connector element 27 at the other end. Connector element 26 removably mates with the percutaneous cable section while connector element 27 unremovably mates with the control unit. Extension cable section 25 is easily sterilizable and has an end-to-end length sufficient to place unremovable connector element 27 outside of the sterile field after mating connector element 26 with the percutaneous cable section. Connector element 26 may comprise any desired type of re-makable connector such as a push-pull Lemo-type connector.

Connector element 27, shown in cross section in FIG. 5, has an overmold covering 30 encasing a push-pull Lemo-type connector 31. Various Lemo-type connectors can be used which are available from LEMO S.A., Ecublens, Switzerland. Connector element 31 includes a release sleeve 32 slidable on a main body 33 wherein a disconnection of the connector is normally made by pulling back on sleeve 32 in order to release element 27 from a mating connector (not shown). In this embodiment, overmold 30 prevents the sliding of sleeve 32 so that once element 27 is pushed onto the main connector, the connection is unremovable (i.e., since sleeve 32 is no longer retractable, there is no means for unlocking the connector). As used herein, unremovable means a condition in which a user is substantially prevented from disconnecting the elements without it being apparent to the user that the connection is intended to be permanent, such as by requiring destruction of the connector.

Figure 7:
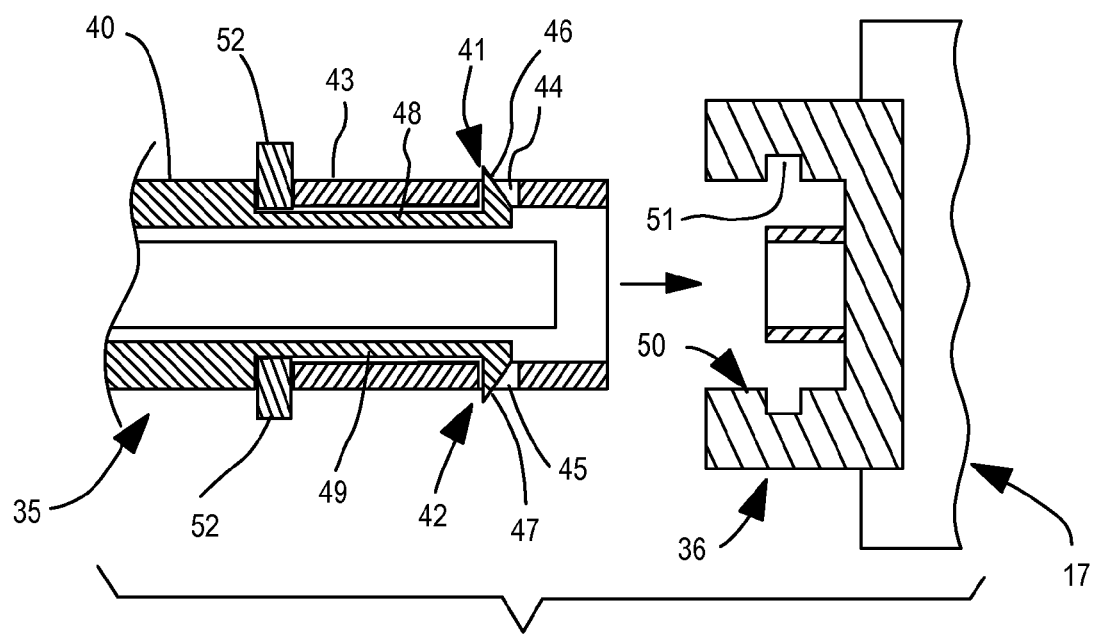
FIG. 7 is a cross-section view showing the interconnection between the control unit and the extension cable.

FIG. 7 shows an embodiment in greater detail having a push-pull Lemo-type connector with a first connector element 35 at the end of the extension cable section and a second connector element 36 contained within control unit 17. For clarity, the internal electrical or other conductors passing through the connector elements and the control unit are not shown. Connector element 35 includes a main body 40 with locking pins 41 and 42 disposed about a peripheral end of main body 40. A tubular outer release sleeve 43 slides along the outside of main body 40 and has openings 44 and 45 receiving ends 41 and 42, respectively. Pins 41 and 42 have angled surfaces 46 and 47 that may be contacted by an axial force in order to deflect respective arms 48 and 49 radially inward to retract pins 41 and 42 into openings 44 and 45. Connector element 36 has a tubular bore 50 sized to receive sleeve 43 and including an inner groove 51 for receiving pins 41 and 42 when connector elements 35 and 36 are mated together. During mating, angled contact surfaces 46 and 47 cause pins 41 and 42 to retract in response to contact with bore 50. Upon full insertion, pins 46 and 47 expand into groove 51 and are captured there for positive latching of the mated connector. For normal disconnection of a Lemo-type connector, a user pulls on sleeve 43 so that the edges of openings 44 and 45 contact surfaces 46 and 47 to retract pins 41 and 41 and remove connector element 35 from connector element 36. In the present invention, an annular ring or disc 52 is fitted over main body 40 within the sliding space normally used by sleeve 43 during retraction. Ring 52 prevents removal of connector element 35 from connector element 36 without preventing the original interconnection. Thus, an unremovable connection is obtained. In a preferred embodiment, both stop ring 52 and an overmold may be employed. Lock ring 52 may be C-shaped with a size adapted to be fitted onto a standard Lemo-type connector so that no other specialized components are required.

Many other kinds of mechanisms can be used for making an unremovable connection. For example, a rotating sleeve could be provided over the electrical connector that threads onto a collar on the control unit, wherein an arrangement of latching pins prevents the sleeve from rotating in the removal direction. Another alternative would be a cover or jacket over the electrical connector with axially-extending hooked fingers that slide into a locking groove in the control unit as the electrical connector is mated.

The present invention achieves improved manufacturing and in-service use by avoiding the need to sterilize a control unit for implantation while maintaining a configuration wherein only one removable cable connection is available when a control unit replacement becomes necessary. The blood pump system of the invention can be made using a process in which a sterilized pump unit is formed and placed by the manufacturer into sterile packaging. Likewise, a percutaneous cable section having a first end connectable to the pump and a second end with a first connector element is formed, sterilized, and placed into sterile packaging. A second or extension cable section is formed having a first end with a second connector element and a second end with a third connector element, wherein the second connector element removably mates with the first connector element. The second cable section is sterilized and placed into sterile packaging. An unsterilized control unit is formed having a fourth connector element that mates with the third connector element such that they will become unremovable after being mated together during the implantation procedure. The pump unit, first cable section, and second cable section in their sterile packaging and the control unit (which does not require sterile packaging) are delivered to a surgical room where implantation is to take place. During the implantation procedure, the first and second connector elements are mated inside the sterile field once the pump is implanted into the patient. The second cable section has a length sufficient to place the third connector element outside of the sterile field where it can be mated with the fourth connector element on the unsterilized control unit.

What is claimed is:

1. A blood pump system comprising:
 a pump configured for implantation in a patient;
 a first cable section configured to pass percutaneously through an incision in the patient having a first end connectable to the pump and having a second end with a first connector element;
 a second cable section having a first end with a second connector element and having a second end with a third connector element, wherein the second connector element removably mates with the first connector element; and
 a control unit having a fourth connector element that mates with the third connector element;
 wherein the first and second cable sections have been sterilized and the control unit is unsterilized; and wherein the third and fourth connector elements are unremovable after being mated.

2. The system of claim 1 wherein the second cable section has a length sufficient to place the third connector element outside of a sterile field during surgical implantation of the pump.

3. The system of claim 1 wherein the third and fourth connector elements include a sliding lock mechanism that opens during mating and then closes to prevent removal thereafter.

4. The system of claim 3 wherein the sliding lock mechanism comprises a push-pull connector system having a slidable release sleeve, wherein the second cable section includes a blocking element to prevent sliding of the release sleeve.

5. The system of claim 4 wherein the blocking element is comprised of a lock ring abutting the release sleeve.

6. The system of claim 4 wherein the blocking element is comprised of an over mold covering the release sleeve.

7. A method of making a blood pump system comprising the steps of:
forming a sterilized pump unit;
placing the sterilized pump in sterile packaging;
forming a sterilized first cable section configured to pass percutaneously through an incision in a patient having a first end connectable to the pump and having a second end with a first connector element;
placing the sterilized first cable section in sterile packaging;
forming a sterilized second cable section having a first end with a second connector element and having a second end with a third connector element, wherein the second connector element removably mates with the first connector element;
placing the sterilized second cable section in sterile packaging; and
forming an unsterilized control unit having a fourth connector element that mates with the third connector element;
wherein after mating of the first and second connector elements inside a sterile field during surgical implantation of the pump into the patient, the second cable section has a length sufficient to place the third connector element outside of the sterile field for mating with the fourth connector element, and wherein the third and fourth connector elements are unremovable after being mated.

* * * * *